US00PP20584P3

(12) United States Plant Patent
Gass

(10) Patent No.: US PP20,584 P3
(45) Date of Patent: Dec. 15, 2009

(54) *CAESALPINIA* PLANT NAMED 'MNSTAMEPA'

(50) Latin Name: *Caesalpinia mexicana×palmeri*
Varietal Denomination: Mnstamepa

(75) Inventor: Ronald E. Gass, Buckeye, AZ (US)

(73) Assignee: Camelot Nurseries, Inc., Glendale, AR (US)

( * ) Notice: Subject to any disclaimer, the term of this patent is extended or adjusted under 35 U.S.C. 154(b) by 60 days.

(21) Appl. No.: 11/998,223

(22) Filed: Nov. 29, 2007

(65) Prior Publication Data

US 2009/0144867 P1 Jun. 4, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP9,516 P 4/1996 Augustine

*Primary Examiner*—Annette H Para
(74) *Attorney, Agent, or Firm*—Jeffrey L. Streets; Streets & Steele

(57) ABSTRACT

A new and distinct hybrid of the genus *Caesalpinia* is provided. This hybrid has been named 'Mnstamepa' for a cultivar name and is trademarked as Sierra Sun™. The new variety is a product of a cross between *Caesalpinia mexicana* and *Caesalpinia palmeri* which occurred in the year 1996. The Genus/species designation for the plant is *Caesalpinia mexicana× palmer.* The new variety was selected because it displays a uniquely different flower color previously unavailable in the genus, and a more open less twiggy habit with a finer leaf structure that either of its parents.

3 Drawing Sheets

Latin name of the genus and species of the plant claimed: *Caesalpinia mexicana×palmeri.*

Varietal denomination

Mnstamepa

BACKGROUND OF THE INVENTION

This cultivar 'Mnstamepa' variety was selected by the inventor as a single plant that was the result of a chance hybrid between an unnamed plant of *Caesalpinia mexicana* with another unnamed plant of *Caesalpinia palmeri.* The *Caesalpinia mexicana* plant and the *Caesalpinia palmeri* plant are unpatented selections originally from native populations. The *Caesalpinia mexicana* is the female parent in the cross that yielded the seedling which is the *Caesalpinia* plant 'Mnstamepa', the subject of this plant patent application.

BRIEF SUMMARY OF INVENTION

The new variety *Caesalpinia* 'Mnstamepa' is distinguishable from its parents by displaying a distinctively different flower color (and other attributes) previously unavailable in the genus *Caesalpinia.* This color is displayed in the drawing marked FIG. 3.

The selected seedling was grown for 20 years after its discovery by asexual propagation carried out in Glendale, Ariz. The new variety reproduces true to type through asexual reproduction. The distinctive habit and flowering characteristic remain constant in each successive crop of grafted plants. The following detailed botanical description is taken from plants that have been growing in containers for at least 12 months. The containers were 24 inch boxes that were irrigated with drip emitters and located outdoors in Glendale, Ariz. in a position of full sun.

The *Caesalpinia*×'Mnstamepa' grew from a chance seedling located along an irrigation canal in Glendale, Ariz., which grew at a moderate growth rate. At an age of 20 years, the tree was observed with an upright growth habit to 5 meters. The new 'Mnstamepa' variety exhibits a more upright character with fewer side branches than the parents to achieve a plant width of 5 meters. The 'Mnstamepa' plant is deciduous at temperature exposures below about 25° F. The maximum winter hardiness is USDA Zone 8.

This hybrid is not known to be susceptible to any soil borne pathogens or to any foliar disease. The plant has not been observed to suffer from any insect infestations.

BRIEF DESCRIPTION OF THE DRAWINGS

The accompanying photographs show typical specimens of plant parts of the new variety in color as nearly true as is reasonably possible to accomplish from conventional photographic procedures.

Figure 1:
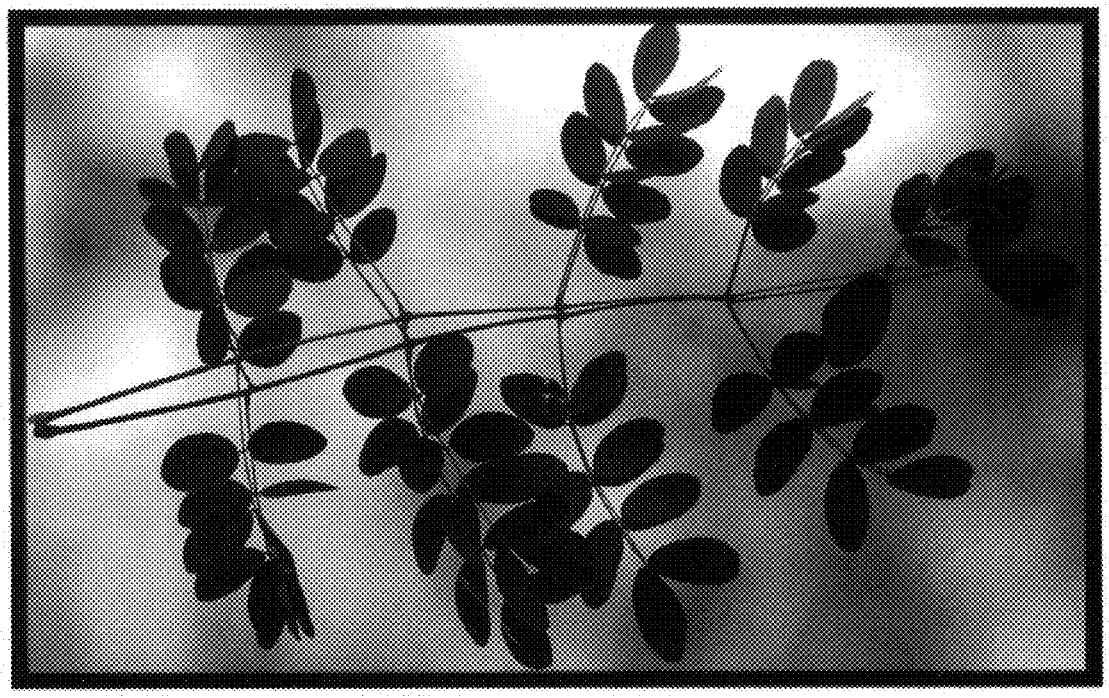
FIG. 1 shows a bipinnately compound leaf in early summer.
Figure 2:
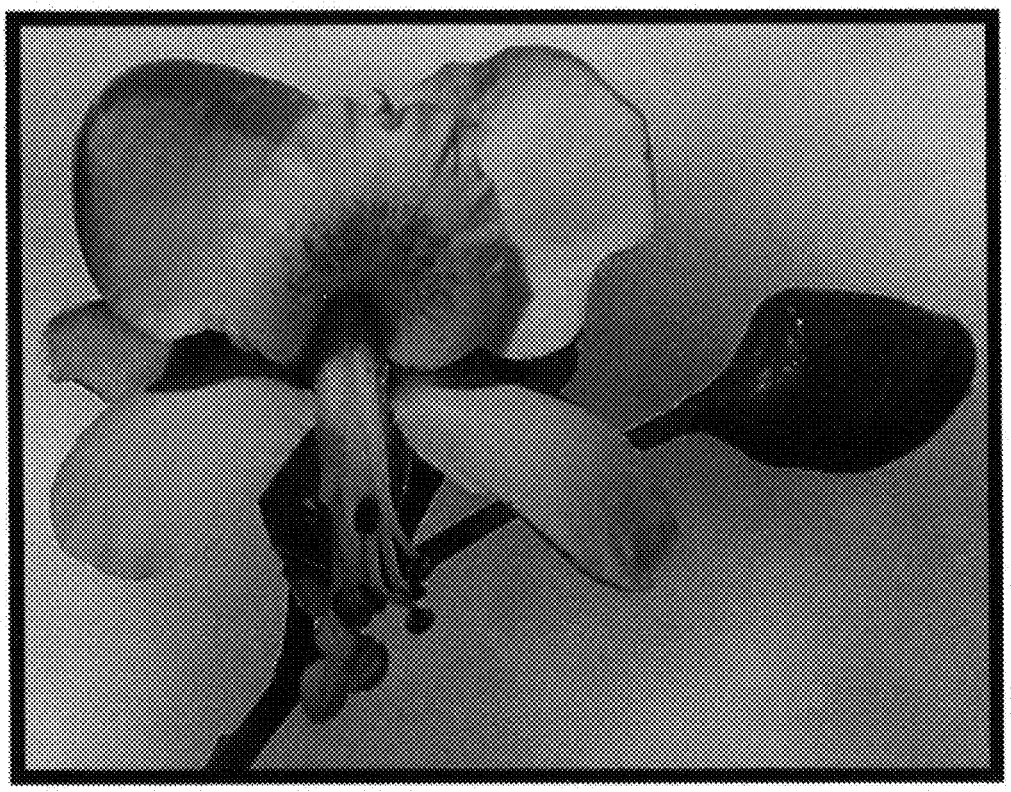
FIG. 2 shows a close up of the flower during the summer season.
Figure 3:
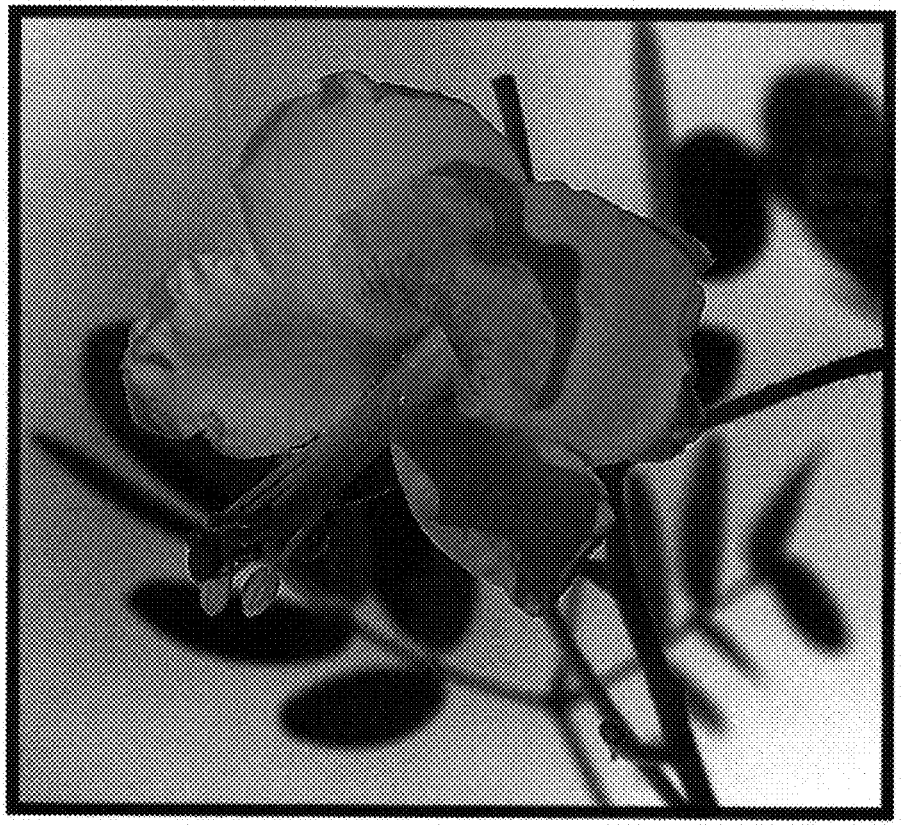
FIG. 3 shows a close up of the flower during the summer season.
Figure 4:
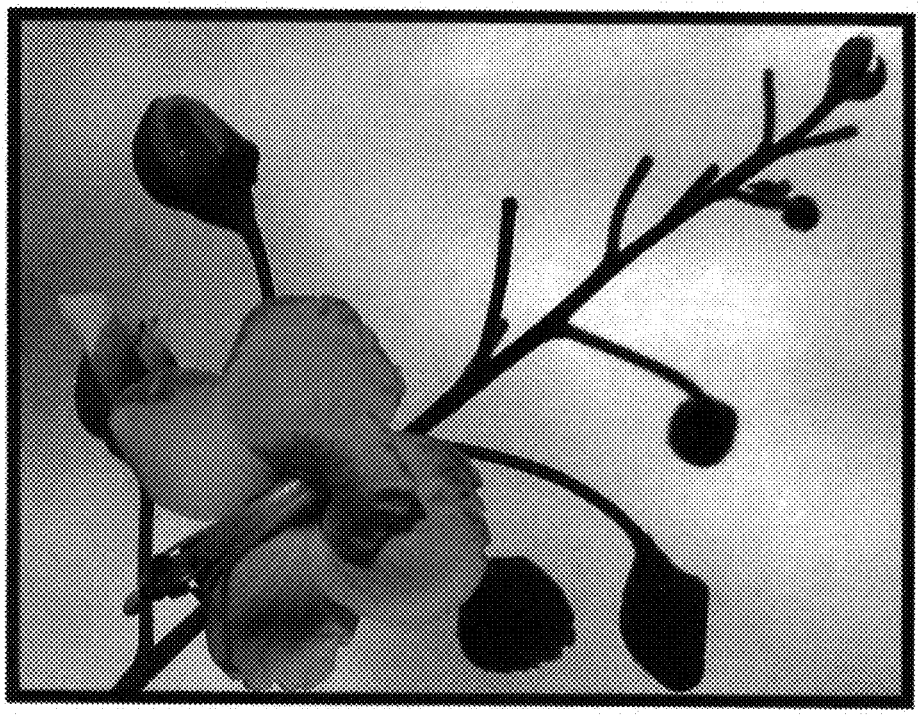
FIG. 4 shows a close up of the inflorescence and individual flower during the summer season.
Figure 5:
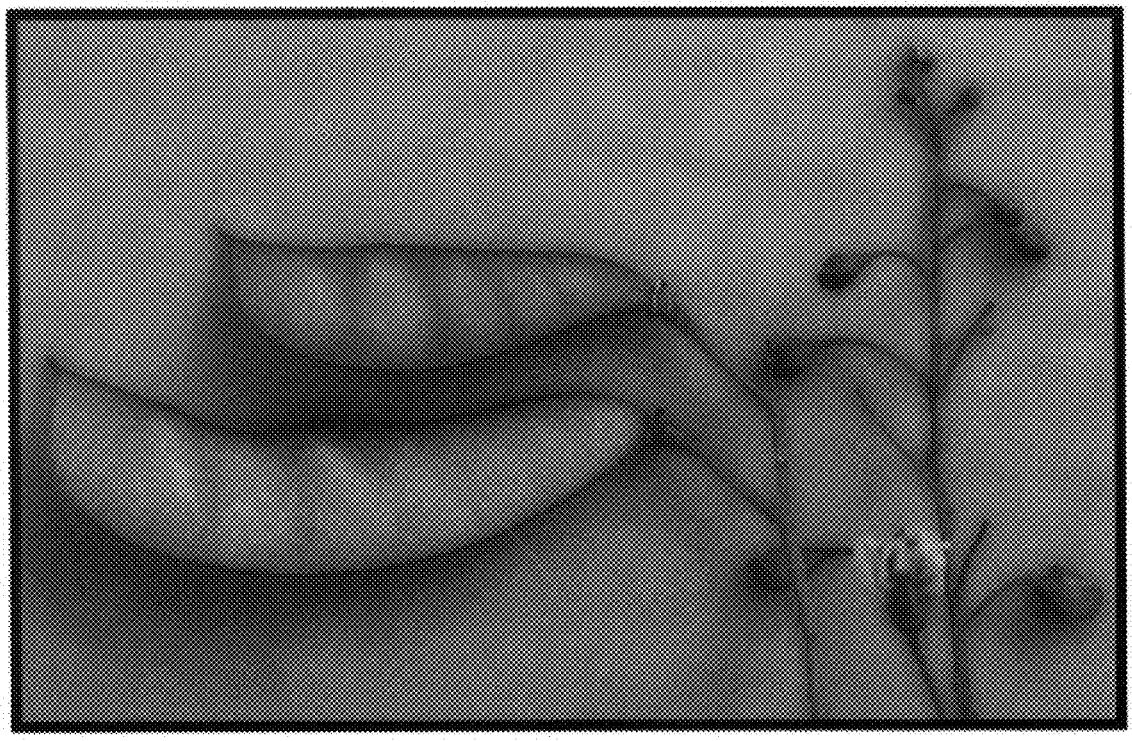
FIG. 5 shows a close up of the fruit.

The color chart used in the identification of colors described herein is The R.H.S. Colour Chart of The Royal Horticultural Society, London, England. The plants described were grown during 2007 at Glendale, Ariz.

DETAILED BOTANICAL DESCRIPTION

Description of the plant:

*Classification.*—*Caesalpinia* Hybrid.
*Plant form.*—Tree.
*Plant height.*—To 5 meters.
*Plant width.*—To 5 meters.
*Plant growth habit.*—Perennial, upright woody tree shrub with open clear trunk similar to *Caesalpinia mexicana* habit.
*Stem/lateral branch diameter.*—2 centimeters.
*Stem/lateral branch internode.*—4 centimeters.

Foliage description:

*Leaf arrangement.*—Alternate.
*Stipules.*—Small.
*Petiole and rachis length.*—25–30 mm.
*Petiole diameter.*—1 mm.
*Petiole color.*—RHS 144A Blushed with RHS 46A.
*Leaf shape.*—Odd bipinnately compound.
*Leaf length.*—Pinnae.—3–4 pairs, 11–12 cm long.
*Leaf width.*—9-10 cm.
*Leaflets.*—Even pinnate; 3–4 pairs; 15–20 mm long, 10 mm wide, rounded-elliptic, to obovate.
*Leaflet base.*—Asymmetrically cuneate.
*Leaflet apex.*—Asymmetrically obtuse.
*Leaflet pubescence.*—Glabrous.
*Leaflet margin.*—Entire.
*Leaflet color.*—RHS 137A.
*Rachis color.*—RHS 144A.
*Stem.*—Distinct lenticels.

Leaves are seasonally uniform in these measurements and colors except in winter when deciduous. Generally deciduous at temperature exposures below 25° F.

Description of the flower:

*Inflorescence type.*—Terminal and axillary raceme to 15 cm with 20–35 flowers.
*Peduncle length.*—15–20 mm.
*Peduncle diameter.*—1 mm.
*Peduncle color.*—RHS 146C blushed with RHS 184B.
*Calyx.*—Pubescent, 5 Sepals RHS 181B striped with RHS 152C on abaxial side, RHS 181B on adaxial side.
*Calyx shape.*—Calyx segments oblong.
*Sepals.*—Oblong 7 mm in length, 4 mm wide.
*Calyx length.*—1 cm.
*Calyx width.*—17–20 mm.
*Calyx pubescence.*—Pubescent.
*Corolla shape.*—Bilaterally symmetrical.
*Corolla height.*—15 mm.
*Corolla diameter.*—22–25 mm.
*Corolla description.*—Banner RHS 9A with large patch of RHS 46C in the center of the adaxial surface. Banner petal 10 mm long and 9 mm wide. Scattered stalked glands on the margin and both surfaces. Wing petals RHS 9A, the claw 2 mm long with stalked glands along the margin; the blade obovate, 7 mm long by 5 mm wide. Keel petal RHS 9A with the claw 2 mm long with stalked glands along the margin; blade obovate, 7 mm long by 5 mm wide.
*Corolla color.*—RHS 13A.
*Corolla pubescence.*—Glabrous.
*Style length.*—11 mm
*Style color.*—RHS 150C.
*Stigma color.*—RHS 165 B.
*Stigma width.*—1 mm.
*Filament number.*—10; distinct, flattened, curved upward, pubescent along the margin, stalked glands present.
*Filament length.*—12–13 mm.
*Filament color.*—RHS 154C.
*Anther length.*—1 mm.
*Anther color.*—RHS 172D.
*Pollen present.*—Yes.
*Pollen color.*—RHS 14A.
*Fruit.*—Oblong acute 6–8 cm glabrous, 15 mm×65 mm, 4–6 seeds.

What is claimed is:

1. A new and distinct variety of *Caesalpinia* plant as herein illustrated and described.

* * * * *